(12) United States Patent
Kang (10) Patent No.: US 10,933,236 B2
(45) Date of Patent: Mar. 2, 2021

(54) APPARATUS FOR STRENGTHENING PELVIC FLOOR MUSCLES

(71) Applicant: FURUN MEDICAL CO., LTD., Wonju-si (KR)

(72) Inventor: Byoung Mo Kang, Wonju-si (KR)

(73) Assignee: FURUN MEDICAL CO., LTD., Wonju-si (KR)

( * ) Notice: Subject to any disclaimer, the term of this patent is extended or adjusted under 35 U.S.C. 154(b) by 90 days.

(21) Appl. No.: 16/313,347

(22) PCT Filed: Jun. 27, 2017

(86) PCT No.: PCT/KR2017/006789
§ 371 (c)(1),
(2) Date: Dec. 26, 2018

(87) PCT Pub. No.: WO2018/004241
PCT Pub. Date: Jan. 4, 2018

(65) Prior Publication Data
US 2019/0160284 A1 May 30, 2019

(30) Foreign Application Priority Data

Jun. 28, 2016 (KR) .................. 10-2016-0081003
Jun. 27, 2017 (KR) .................. 10-2017-0080915

(51) Int. Cl.
*A61N 1/36* (2006.01)
*A61N 1/04* (2006.01)
(Continued)

(52) U.S. Cl.
CPC .......... *A61N 1/36007* (2013.01); *A61B 5/002* (2013.01); *A61B 5/202* (2013.01);
(Continued)

(58) Field of Classification Search
CPC .............. A61N 1/36007; A61N 1/0452; A61N 1/36031; A61N 1/3603; A61N 1/0476;
(Continued)

(56) References Cited

U.S. PATENT DOCUMENTS

2009/0082617 A1* 3/2009 Vecchiotti ............. A61F 2/0045
600/30
2013/0123767 A1* 5/2013 Clark, III ......... A61B 17/32002
606/13
(Continued)

FOREIGN PATENT DOCUMENTS

KR      20-0345464       3/2004
KR    10-2012-0037859    4/2012
(Continued)

OTHER PUBLICATIONS

International Search Report for International Application No. PCT/KR2017/006789, dated Nov. 9, 2017.
(Continued)

*Primary Examiner* — Amanda K Hulbert
*Assistant Examiner* — Natasha Patel
(74) *Attorney, Agent, or Firm* — Kile Park Reed & Houtteman PLLC (57) ABSTRACT

The present invention relates to an apparatus for strengthening pelvic floor muscles which can be used even when a user wears clothes and thus can be used comfortably without psychological burden; can be cleanly used without the remains of foreign matter around the urethra and the anus or on the exterior of the apparatus after use; can perform treatment in a state in which an electrode portion is pressed in close contact with the bladder and the pelvic floor muscles through a height adjustment means; and can perform both an active exercise through low-frequency pulses and a passive exercise through a muscular strength sensing means.

2 Claims, 6 Drawing Sheets

(51) Int. Cl.
  *A61B 5/00* (2006.01)
  *A61B 5/22* (2006.01)
  *A61B 5/20* (2006.01)

(52) U.S. Cl.
  CPC ............ *A61B 5/227* (2013.01); *A61B 5/4836* (2013.01); *A61N 1/0452* (2013.01); *A61B 5/7475* (2013.01); *A61N 1/0476* (2013.01); *A61N 1/0484* (2013.01); *A61N 1/3603* (2017.08); *A61N 1/36031* (2017.08)

(58) Field of Classification Search
  CPC ................ A61N 1/0484; A61N 1/0492; A61N 1/36014; A61N 1/36107; A61N 1/0472; A61N 1/08; A61B 5/002; A61B 5/227; A61B 5/202; A61B 5/4836; A61B 5/7475; A61B 5/20; A61B 5/4519
  See application file for complete search history.

(56) References Cited

U.S. PATENT DOCUMENTS

| | | | |
|---|---|---|---|
| 2013/0217954 A1* | 8/2013 | Danna | A61B 17/06109 600/30 |
| 2015/0290450 A1* | 10/2015 | Kolb | A61N 1/36014 607/41 |
| 2016/0270727 A1* | 9/2016 | Berg | A61B 5/0006 |

FOREIGN PATENT DOCUMENTS

| KR | 10-2014-0103694 | 8/2014 |
|---|---|---|
| KR | 10-2014-0116596 | 10/2014 |

OTHER PUBLICATIONS

Written Opinion for International Application No. PCT/KR2017/006789, dated Nov. 9, 2017.

\* cited by examiner

APPARATUS FOR STRENGTHENING PELVIC FLOOR MUSCLES

TECHNICAL FIELD

The invention relates to an apparatus for strengthening pelvic floor muscles to strengthen a pelvic floor muscle for treatment of urinary incontinence, fecal incontinence or others by strengthening a pelvic floor muscle, and more particularly to an apparatus for strengthening pelvic floor muscles which user can use easily as he/she wearing clothes without psychological burden, can use cleanly because no foreign materials remain around urethra, anus and the outer surface of the apparatus after using it, can treat a pelvic floor muscle with electrodes being pressed against a bladder and a pelvic floor muscle by a height adjusting means, and can enhance treating effect by implementing both a passive exercise through low frequency pulse and an active exercise through a muscular strength sensor.

BACKGROUND ART

Generally, a urinary incontinence is a disease in which urine leaks against a patient's will, and patients as much as 30~40% of adult women suffer, but they are unwilling to expose it, so only about 23% of the patients go to the doctor. Accordingly, if a treatment apparatus in this field can be used easily without feeling shame and psychological burden to provide various treatments, it will satisfy the increasing demands in accordance with a recent population aging trend.

The conventional treatment apparatuses for urinary incontinence are mainly inserting type which is to be inserted into a vagina of user and applies low frequency pulse, but it is very inconvenient and causes humiliation of user. In order to solve this problem of inserting type apparatus, a cushion type treatment apparatus was developed, which is provided with electrodes on the center of the cushion, and if user sits on the electrodes with taking off clothes, low frequency pulse is applied on the pelvic floor muscle of user and a passive exercise is induced. This cushion type apparatus can solve the problem related with inserting into a vagina, but it still requires user to take off underwear and sit on the cushion for her perineum to contact on the electrodes. Therefore, the user still has to take off his/her clothes in the private place and use the apparatus privately, and it may still incur humiliation.

And, the conventional low frequency treatment apparatuses are used as conductive material of cream or gel type being applied on the electrodes of the apparatus. But it is inconvenient because foreign materials remaining on the apparatus should be cleaned after using it. If the conductive material is not used, then electric stimulus cannot be effectively transmitted to the body, or the electric stimulus could be transmitted irregularly, which may incur pricking to user.

In addition, the conventional low frequency treatment apparatuses are to contract and relax pelvic floor muscles passively by means of low frequency pulse, which increases elasticity of muscle, but it cannot increase strength of muscle sufficiently. In order to increase strength of muscle, an active exercise is necessary in which user should contract and relax his/her muscle directly. Therefore, a passive exercise thorough low frequency pulse has a limit to increase strength of muscle satisfactorily.

DISCLOSURE

Technical Problem

The invention is proposed to solve the above problems, and the object of the invention is to provide a to an apparatus for strengthening pelvic floor muscles which a user can use easily as he/she wearing clothes without psychological burden, can use cleanly as no foreign materials remain around urethra, anus and the outer surface of the apparatus after using it, can treat a pelvic floor muscle with electrodes being pressed against a bladder and a pelvic floor muscle by a height adjusting means, and can enhance treating effect by implementing both a passive exercise through low frequency pulse and an active exercise through a muscular strength sensing means

Technical Solution

According to an aspect of the invention, there is provided an apparatus for strengthening pelvic floor muscles which comprises:

a body 10 of elongated shape to be placed inside an underwear I for user to sit on by perineum;

electrodes 20 positioned on the upper side of the body 10 to apply electric stimulus on the perineum of user;

a flexible cover 30 provided on both sides of the body 10 and bendable to form a gap between the body 10 into which a conductive sheet S is tucked and clamped wherein;

the conductive sheet S covers the electrodes 20 to enhance the transmission of electric stimulus to user, and the ends of the conductive sheet S is placed inside the flexible cover 30 not to contact the underwear I of user and so it can used cleanly and neatly, and contamination around urethra and anus of user or the apparatus itself can be prevented by only replacing the conductive sheet 3.

According to the other aspect of the invention, there is provided an apparatus for strengthening pelvic floor muscles wherein; the conductive sheet S is a wet sheet in which moisture is impregnated.

According to the other aspect of the invention, there is provided an apparatus for strengthening pelvic floor muscles wherein; the body 10 includes a upper body 11 on the upper side of it, a support 15 on the lower side of it, and a height adjusting means 50 between the upper body 11 and the support 15 to lift the upper body 11 to a desired height, the height adjusting means 50 being capable of further pressing the electrodes 20 of the upper body 11 against the bladder and a pelvic floor muscle P of user and applying a low frequency pulse.

According to the other aspect of the invention, there is provided an apparatus for strengthening pelvic floor muscles wherein; the height adjusting means 50 includes a first thread member 53 extending upright from the support 15, a second thread member 51 extending downward from the upper body 11 and being engaged with the first thread member 53, a recess 16 formed on the bottom side of the support 15, and a handle 55 positioned in the recess 16 and connecting with the first thread member 53, the handle 55 not being projected downward from the support 15, so supporting the body 10 stably and turning easily to adjust the height of the body 10.

According to the other aspect of the invention, there is provided an apparatus for strengthening pelvic floor muscles which comprises:

a body 10 of elongated shape to be placed inside an underwear I for user to sit on by perineum;

electrodes 20 positioned on the upper side of the body 10 to apply electric stimulus on the perineum of user;

a base plate 40 engaged with the lower part of the body 10 so that the end of a conductive sheet S should be placed and clamped between the body 10 and the base plate 40; wherein the conductive sheet S covers the electrodes 20 to enhance the transmission of electric stimulus to user, and the ends of the conductive sheet S is covered by the base plate 40 not to contact the underwear I of user so it can used cleanly and neatly, and contamination around urethra and anus of user or the apparatus itself can be prevented by only replacing the conductive sheet 3.

According to the other aspect of the invention, there is provided an apparatus for strengthening pelvic floor muscles wherein; magnets 60 are attached on the body 10 and the base plate 40 in the corresponding positions to maintain engaging state by magnetic force, the magnets 60 being capable of fixing the conductive sheet 3 inserted between the body 10 and the base plate 40 firmly.

According to the other aspect of the invention, there is provided an apparatus for strengthening pelvic floor muscles wherein; the body 10 includes a upper body 11 on the upper side of it, a support 15 on the lower side of it, and a height adjusting means 50 between the upper body 11 and the support 15 to lift the upper body 11 to a desired height, the height adjusting means 50 being capable of further pressing the electrodes 20 of the upper body 11 against the bladder and a pelvic floor muscle P of user and applying a low frequency pulse.

According to the other aspect of the invention, there is provided an apparatus for strengthening pelvic floor muscles wherein; the height adjusting means 50 includes a first thread member 53 extending upright from the support 15, a second thread member 51 extending downward from the upper body 11 and being engaged with the first thread member 53, a recess 16 formed on the bottom side of the support 15, and a handle 55 positioned in the recess 16 and connecting with the first thread member 53, the handle 55 not being projected downward from the support 15, so supporting the body 10 stably and turning easily to adjust the height of the body 10.

According to the other aspect of the invention, there is provided an apparatus for strengthening pelvic floor muscles which comprises:

an upper body 11 of elongated shape for user to sit on by perineum;

electrodes 20 positioned on the upper body 11 to apply electric stimulus on the perineum of user;

a support 15 supporting the upper body 11 in the manner that, if user sits on the upper body 11, the upper body 11 should lift the center of pelvic floor muscle P of user and invert it in 'n' shape;

a muscular force sensor 70 on the upper or lower part of the support 15 to sense force or pressure which presses the upper body 11 down by the muscular contraction when user contracts his/her inverted pelvic floor muscle P; and a controller 80 to process data of the force or pressure sensed by the muscular force sensor 70 and transmit the data outward to display them; wherein the user can select between a passive electric stimulus through the electrodes 20 and an active muscular exercise through the muscular force sensor 70.

According to the other aspect of the invention, there is provided an apparatus for strengthening pelvic floor muscles, wherein a height adjusting means 50 is further provided between the upper body 11 and the support 15 to adjust the height of the upper body 11 to a desired height so that the press intensity against the pelvic floor muscle P of user can be easily adjusted by the height adjusting means 50.

According to the other aspect of the invention, there is provided an apparatus for strengthening pelvic floor muscles which comprises:

an upper body 11 of elongated shape 1 for user to sit on by perineum;

a support 15 supporting the upper body 11 in the manner that, if user sits on the upper body 11, the upper body 11 should lift the center of pelvic floor muscle P of user and invert it in 'n' shape;

a height adjusting means 50 positioned between the upper body 11 and the support 15 to adjust the height of the upper body 11, so that the press intensity against the pelvic floor muscle P of user can be adjusted;

a muscular force transmitter 75 connected to the upper end or lower end of the height adjusting means 50 and being parallel with the upper body 11;

a muscular force sensor 70 connected to the front end and rear end respectively to sense force or pressure which presses the upper body 11 down by the muscular contraction when user contracts his/her inverted pelvic floor muscle P; and a controller 80 to treat data of force or pressure sensed by the muscular force sensor 70 and transmit the data outward to display them.

Advantageous Effect

According to the invention, the user can use the apparatus while he/she wears clothes without psychological burden, and it can solve the problem of inconvenience in using with taking off clothes in the private place.

And, by covering the moisture impregnated conductive sheet S on the upper of the body 10, electric stimulus can be effectively transmitted to perineum of user, and as there is no need to apply conductive material of cream or gel type on the electrodes of the apparatus, no foreign materials remain around urethra, anus and the outer surface of the apparatus after using it, so it is possible to use cleanly and neatly.

In addition, though moisture impregnated conductive sheet S is covered on the body 10, the end of the conductive sheet S is tucked into the flexible cover 30 or the base plate 40 and the underwear I may not be wet, so it can be used cleanly and comfortably. And the conductive sheet S does not rise from the body 10 and it is neatly clamped by the flexible cover 30 or the base plate 40, it is easy to insert the apparatus into the clothes of user.

And, as there is provided a height adjusting means 50 to adjust the electrodes 20 on the body 10 to a desired height, it is possible to apply low frequency pulse as the electrodes 20 being pressed against the bladder and the pelvic floor muscle P tightly depending on the feature of user body, so it will enhance the conductivity on the target area of user body.

And, as it is possible to implement both a passive exercise through low frequency pulse and an active exercise through a muscular force sensor, the recovering effect of pelvic floor muscle P can be highly increased.

And, as the apparatus according to the invention is to be used in the perineum inside the underwear of user, the size of the apparatus can be made small and compact, so it is easily carried, and the structure of the apparatus is simple, so the manufacturing cost will be much reduced.

DETAILED DESCRIPTION OF THE INVENTION

Hereinafter, the preferred embodiments of the invention will be described with reference to the drawings. FIG. 1 to FIG. 6 show various embodiment of the invention.

Figure 1:
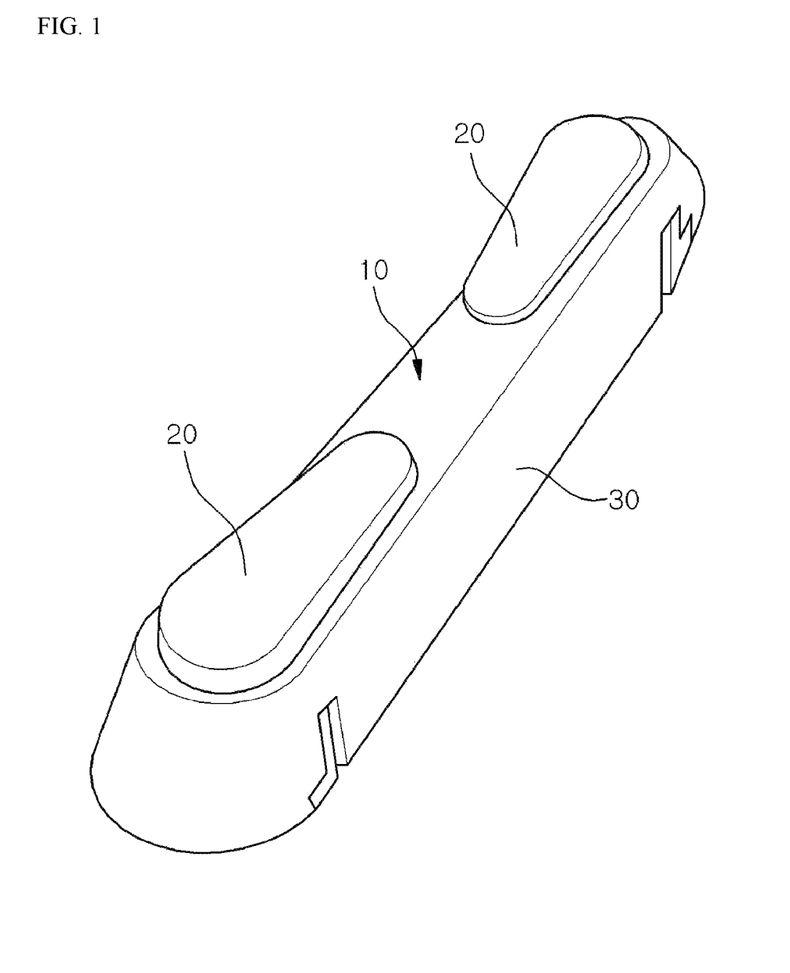
FIG. 1 is a perspective of the embodiment of the invention
Figure 2:
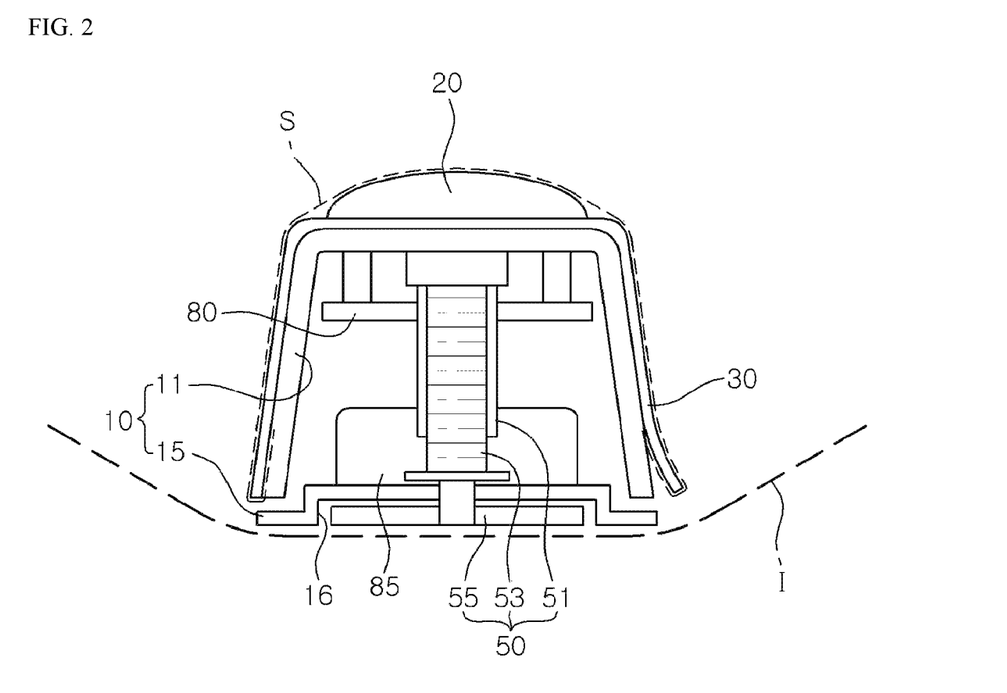
FIG. 2 is a front sectional view of the embodiment of the invention

Referring FIG. 1 and FIG. 2, one embodiment of the invention includes a body 10 of elongated shape to be placed inside an underwear I for user to sit on by perineum, two or more electrodes 20 positioned on the upper side of the body 10 to apply electric stimulus on the perineum of user and a flexible cover 30 positioned on both sides of the body 10 and bendable to form a gap between the body 10 into which a conductive sheet S is tucked and clamped.

The body 10 is elongated with narrow width to be inserted inside the underwear I for user to sit on by perineum, and it comprises an upper body 11 on the upper side of it and a support 15 on the lower side of it. A controller 80 is provided between the upper body 11 and the support 15, a cushion of silicon material is provided on the surface of the upper body 11. A height adjusting means 50 is further provided between the upper body 11 and the support 15 to lift the upper body 11 to a desired height so that the electrodes 20 can be positioned further adjacent to and pressed against the bladder and the pelvic floor muscle P, then a low frequency pulse is applied.

The height adjusting means 50 includes a first thread member 53 extending upright from the support 15, a second thread member 51 extending downward from the upper body 11 and being engaged with the first thread member 53, a recess 16 formed on the bottom side of the support 15, and a handle 55 positioned in the recess 16 and connecting with the first thread member 53, the handle 55 not being projected downward from the support 15, so supporting the body 10 stably on the floor and turning easily to adjust the height of the body 10.

The electrodes 20 comprises at least two electrodes exposed on the upper surface of the body 10 and installed separately in the longitudinal direction to contact the front and rear area of perineum of user and apply a low frequency pulse on the pelvic floor muscle P to induce a passive exercise. The electrodes 20 are made of conductive material such as metal or carbon-mixed silicon for the effective transmission of low frequency pulse supplied from the controller 80 to the user body.

The flexible cover 30 is made of silicon band to be fitted around the body 10, or it is made of flexible plate to be attached on both sides of the body 10. The lower end of the flexible cover 30 can be bent to form a gap between the body 10, into which both ends of the conductive sheet S can be tucked and clamped neatly.

The conductive sheet S is covered on the electrodes 20 of the body 10 to transmit low frequency pulse from the electrodes 20 to user body smoothly and effectively, and preferably it can be a wet paper or a moisture-impregnated tissue. That is, the sheet itself need not be conductive material and conductivity may come from added material such as water impregnated in the sheet, and the water may or may not contain electrolyte.

The conductive sheet S can transmit low frequency pulse from the electrodes 20 to perineum of user effectively and smoothly, and additional conductive cream or gel need not be applied on the electrodes 20, so it can be used cleanly without remaining cream or gel around urethra, anus or the apparatus itself, and it is advantageous that, if only the conductive sheet S is replaced, urethra, anus or the apparatus itself can be prevented from being contaminated by foreign materials.

The controller 80 is connected to the inner battery 85 to supply a low frequency pulse to the electrodes 20 and includes a micom, a generator of low frequency pulse and communication module, and it can be connected to outer apparatuses such as smartphone, computer or remote controller so that signal can be communicated, and operation state of the apparatus can be displayed.

The operation of the above embodiment of the invention will be described.

In this embodiment, a moisture-impregnated conductive sheet S is covered on the electrodes 20 of the body 10, and both ends of the conductive sheet S is inserted into gap between the body 10 and the flexible cover 30, then the conductive sheet S covered on the body 10 is tucked into the flexible cover 30, so it is neatly arranged and clamped. Then the conductive sheet S will cover the upper and side surface of the body 10 and it does not contact the underwear I of user directly, so it can be used cleanly and neatly.

Then, the body 10 of the apparatus is inserted inside the underwear I of user and is positioned on perineum of user, and the user sits it on, then the perineum is lifted by the height of the body 10 and is pressed against the body 10. And the height adjusting means 50 provided in the body 10 is used to adjust the height of the apparatus 10 according to the feature of user body, so the electrodes 20 can be tightly pressed against the targeted bladder and pelvic floor muscle P, then a low frequency pulse may be applied, so the conductivity of the targeted body area can be enhanced.

User can input signals such as frequency, intensity, time to the controller 80 through smartphone, computer, remote controller, then desired low frequency pulse can applied on the pelvic floor muscle of user while he/she wears clothes, and it will be very convenient, and anybody can use it at ease.

And, a conductive sheet S such as wet tissue is covered on the upper part of the body 10, so low frequency pulse will be effectively and smoothly transmitted from the electrodes 2o to perineum of user, and by replacing the conductive sheet S, the apparatus itself can be prevented from being contaminated by secretion of urethra and anus, and contamination around urethra and anus by remaining foreign material such as cream or gel type conductive agent can be prevented. And the conductive sheet S such as wet tissue is much cheaper than conventional gel type electrode pad.

Figure 3:
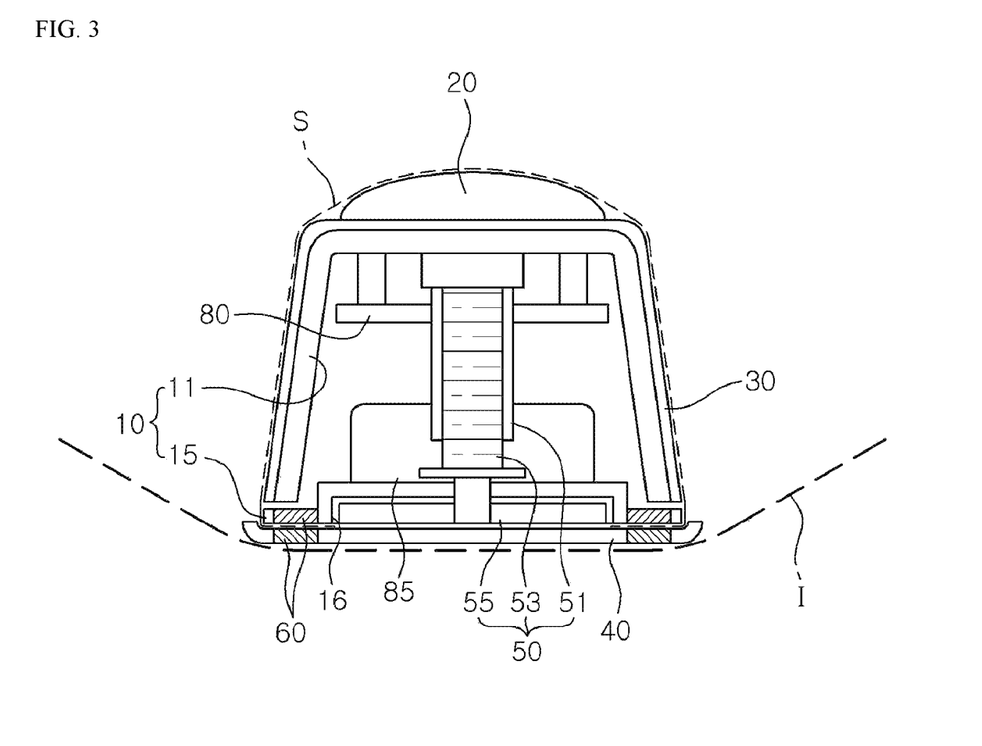
FIG. 3 is a front sectional view of anther other embodiment of the invention

Another embodiment of the invention, as shown in FIG. 3 is similar to the above first embodiment in that it includes a body 10 of elongated shape to be placed inside an underwear I for user to sit on by perineum, electrodes 20 provided on the upper side of the body 10 to apply low frequency pulse on the perineum of user, a conductive sheet S covered on the electrodes 20 and a height adjusting means 50 to press the electrodes 20 against the bladder and pelvic floor muscle tightly.

But the second embodiment of the invention includes a base plate 40 detachably mounted on the lower side of the body 10, so both ends of the conductive sheet S covered on the body 10 should be placed between the body 10 and the base plate 4, and it can be clamped by the base plate 40. And magnets 60 are attached on the body 10 and the base plate 40 in the corresponding positions to maintain engaging state by magnetic force, then the conductive sheet 3 inserted between the body 10 and the base plate 40 can be fixed firmly.

The operation of this embodiment of the invention is explained below. The conductive sheet S such as wet tissue is covered on the upper and side of the body 10 so that both end of the conductive sheet S are placed on the bottom of the apparatus, then the bottom of the body 10 is covered by the base plate 40, then the end of the conductive sheet S is covered by the base plate 40 and does not contact the underwear I, so the underwear I may not get wet and be used cleanly. Then the base plate 40 can be fixed on the body 10 firmly by the magnet 60.

Then, the user inserts the body 10 of the apparatus inside his/her underwear and sit it on, and adjust the frequency, intensity, time and others by outer device such as smartphone, computer, so it can be use conveniently and at ease while user wears clothes. And the electrodes 20 can be pressed against the bladder and pelvic floor muscle by height adjusting means 50, so the conductivity on the target body area can be enhanced.

Figure 4:
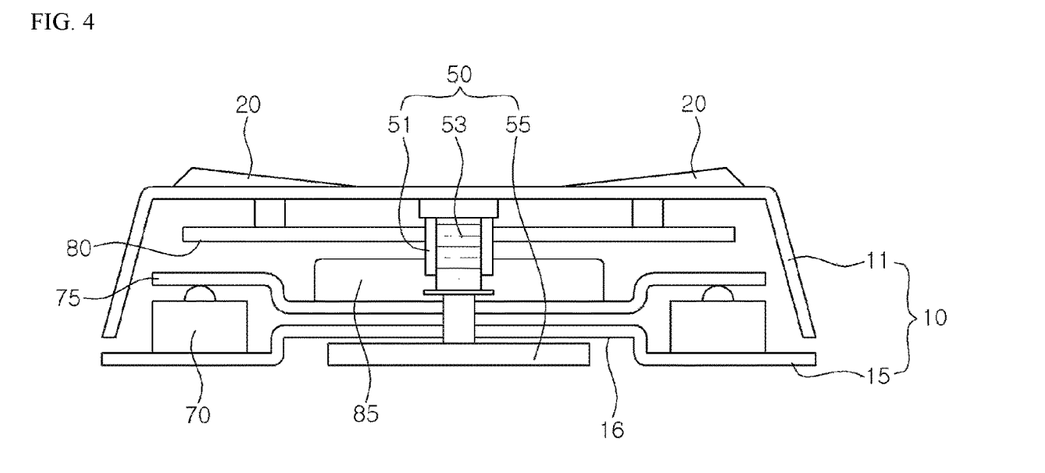
FIG. 4 is a side sectional view of another embodiment of the invention
Figure 5:
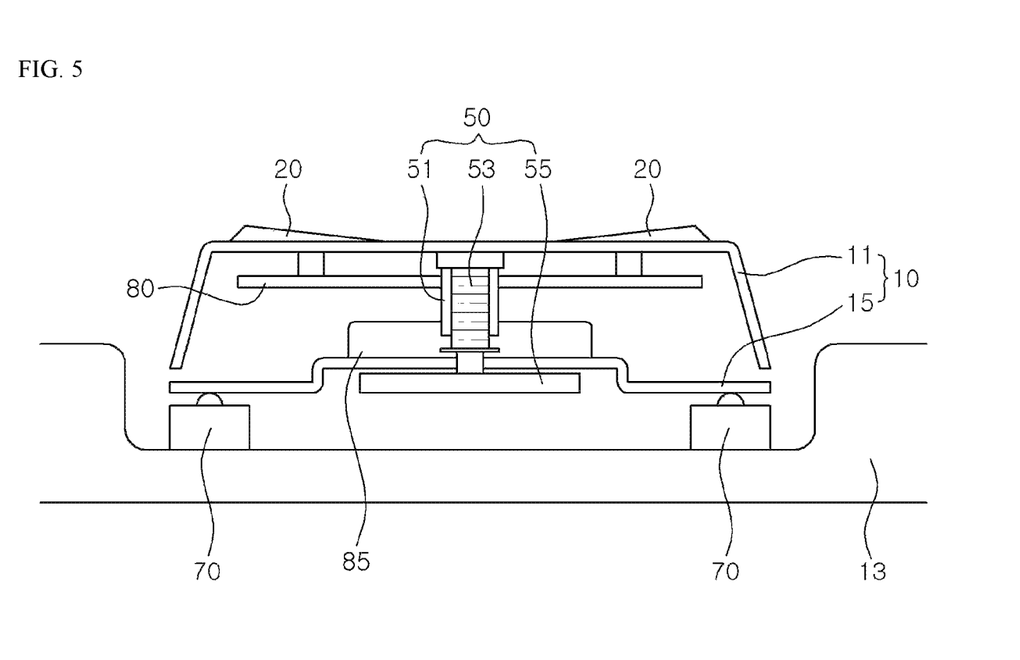
FIG. 5 is a side sectional view of another embodiment of the invention
Figure 6:
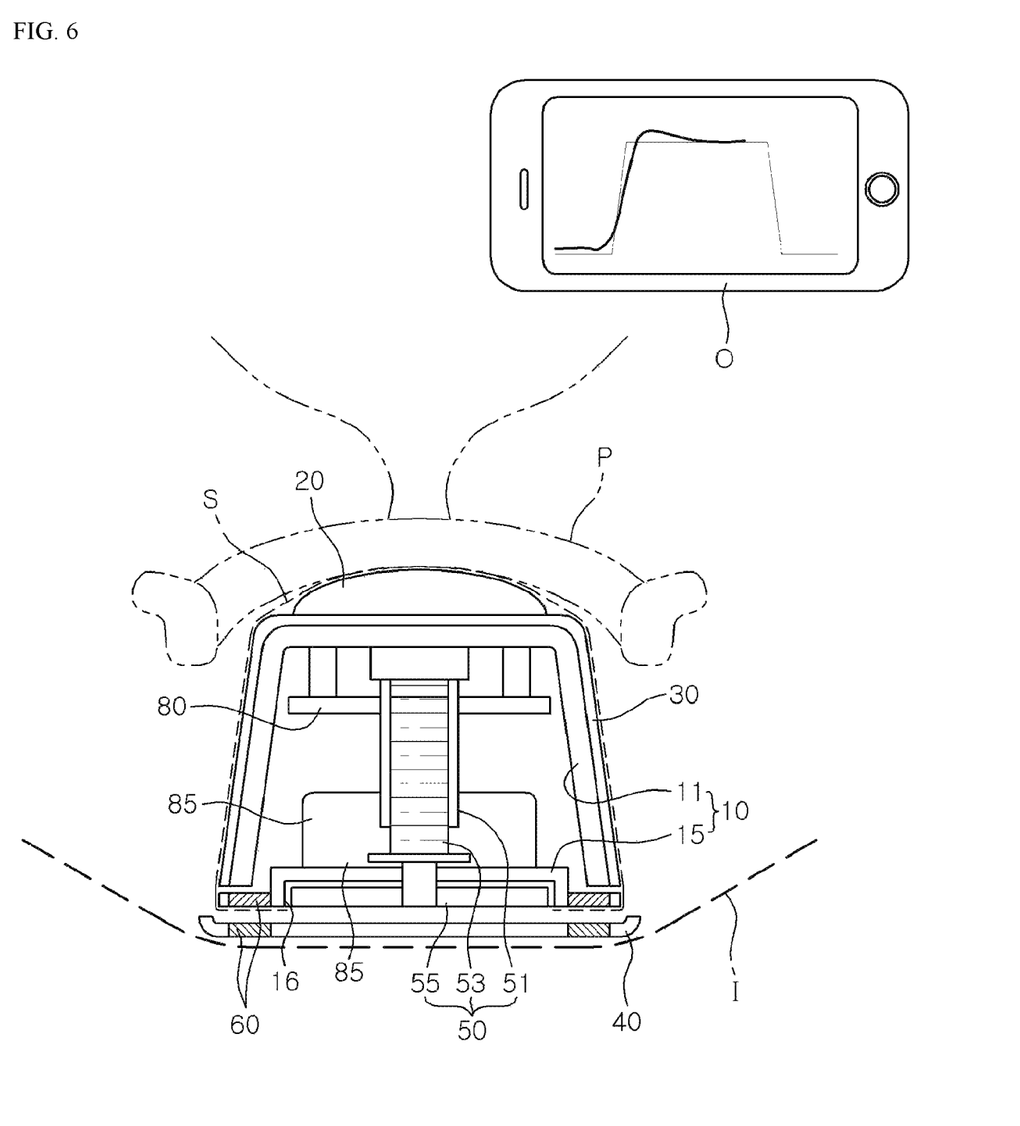
FIG. 6 is a front sectional view of another embodiment of the invention

Another embodiment of the invention, as shown in FIG. 4 to FIG. 6 includes an upper body 11 of elongated shape for user to sit on by perineum, electrodes 20 provided on the upper body 11 to apply electric stimulus on the perineum of user, a support 15 supporting the upper body 11 in the manner that, if user sits on the upper body 11, the upper body 11 should lift the center of pelvic floor muscle P of user and invert it in 'n' shape, a muscular force sensor 70 on the upper or lower part of the support 15 to sense the force or pressure which presses the upper body 11 down by the muscular contraction when user contracts his/her inverted pelvic floor muscle P, and a controller 80 to process data of the force or pressure sensed by the muscular force sensor 70 and transmit the data outward to display them, and the user can select between a passive electric stimulus through the electrodes 20 and an active pelvic floor muscular contraction exercise through the muscular force sensor 70.

A height adjusting means 50 is further provided between the upper body 11 and the support 15 to adjust the upper body 11 to a desired height, so the intensity of strength pressing against the pelvic floor muscle of user can be easily adjusted by the height adjusting means 50.

The upper body 11, the electrodes 20 and the height adjust means 50 of the embodiment are similar to those of the above embodiment, so detailed explanation will be omitted. As shown in FIG. 4, a muscular force sensor 70 is installed between the upper body 11 and the support 15, and a muscular force transmitter 75 is installed on top of the muscular force sensor 7o, and the muscular force transmitter 75 is connected to the upper or lower end of the height adjusting means 50 horizontally. This muscular force transmitter 85 is placed in parallel to the upper body 11 and connected to the muscular force sensor 70 at the front and rear end. If the muscle transmitter 75 is positioned under the height adjusting means 50, then the muscular force sensor 70 may be positioned between the muscle transmitter 75 and the support 15, but if the muscle transmitter 75 is installed on top of the height adjusting means 50, then the muscular force sensor 70 can be installed between the muscle transmitter 75 and the upper body 11.

As shown in FIG. 5, the muscular force sensor 70 may be installed under the base plate 15 and on the cushion type bottom plate 13, in which case the body 10 of the apparatus comprises of upper body 11 and the bottom plate 13, and the base plate 15 can be regarded to do the same function with the muscle transmitter 75 of the above embodiment.

The muscular force sensor 70 and the muscular force transmitter 75 function to support the upper body 11 to lift the central area of pelvic floor muscle P and invert it in 'n' shape. If the bottom plate 13 is provided, even though the upper body 11 is pressed down by the contraction of pelvic floor muscle P, the press can be supported firmly on the wide area of the rigid bottom plate 13, so the contraction force of the pelvic floor muscle transmitted through the muscle force sensor 70 can not be damped and detected correctly. That is, even though the apparatus is used as being placed on the soft cushion, the wide area of rigid bottom plate 13 can support the upper body 11 sufficiently and firmly, so the contraction force of the pelvic floor muscle P can be detected by the muscular force sensor 70 correctly without error.

The muscular force sensor 70 is a sensor to detect the contraction force of pelvic floor muscle P by force or press unit, and if user sits on the body 10 as shown in FIG. 6, the pelvic floor muscle P is lifted by the body 10 to be inverted in 'n' shape. In this state, the user contracts his/her lifted pelvic floor muscle P, then normal component of force due to the contraction of pelvic floor muscle P is transmitted through the body 10 to the muscular force sensor 70, and the muscular force sensor 70 transmits the sensed signal to the controller 80.

The controller 80 is connected to the inner battery 85 to apply low frequency pulse and process data of contraction force sensed by the muscular force sensor 70 and transmit them to buzzer, smartphone, computer or other outer devices. Accordingly, the user can recognize the extent of contraction and relaxation of pelvic floor muscle P by ear and eyes through buzzer, smartphone or computer and can continue the active exercise of pelvic floor muscle contraction interestingly.

The operation of the above embodiment of the invention is explained below.

As shown in FIG. 6, a moisture-impregnated conductive sheet S is covered on the upper and side of the body 10 so that the ends of the conductive sheet S are placed on the bottom of apparatus, then the bottom of the body 10 is covered by the base plate 40. And, the user inserts the body 10 inside the underwear and sits it on. Then the user can adjust the frequency, intensity or time though the outer device 0 such as smartphone and computer, and the user can do a passive exercise of pelvic floor muscle P by use of low frequency pulse. And the user can easily adjust the pressing extent of electrodes 20 through the height adjusting means 50 according to the user body feature.

According to the embodiment of the invention, the pelvic floor muscle P of the user will be lifted to be inverted in 'n' shape, then the user contracts his/her pelvic floor muscle P, then normal component of force due to the contraction of pelvic floor muscle P is transmitted through the upper body 11 to the muscular force sensor 70 in FIG. 4 or FIG. 5, and the signal is processed in the controller 80 and transmitted to buzzer, smartphone, tablet PC, computer or other devices, so that the extent of contraction and relaxation of pelvic floor muscle P can be recognized and checked by the eye or ear of user, and the user can continue the active muscle exercise interestingly.

It is not easy for the user to sit on the center of the upper body 11 exactly, so the user may sit biasedly toward one of front and rear side. In this case, as the muscular force sensors 70 are installed on both the front and rear end of the muscle transmitter 75, correct sensing value can be obtained by adding the two values of both the sensors 70 regardless of the sitting position.

The pelvic floor muscle P is not used ordinarily, so user may feel difficulty to contract the pelvic floor muscle even though the user gets trained. But if the user can recognize and confirm the extent of contraction and relaxation of the pelvic floor muscle P, then he/she can easily learn or master the skill how to contract and relax the pelvic floor muscle P, therefore this will be an effective exercise method.

As described above, according to the invention, both the passive exercise through low frequency pulse and an active muscle exercise through the muscular force sensor 70 can be carried out selectively to enhance the recovery effect of the pelvic floor muscle P highly. The invention is mainly to strengthen and recover the pelvic floor muscle P easily and effectively, and it can be used to heal urinary incontinence, constipation in related with pelvic muscular trouble, fecal incontinence, sexual function improvement, prostate disease and others, and all these will be included in the scope of the invention.

The invention claimed is:

1. An apparatus for strengthening pelvic floor muscles which comprises:
   an upper body of elongated shape for a user to sit on by perineum;
   electrodes positioned on the upper body to apply electric stimulus on the perineum of the user;
   a support supporting the upper body in the manner that, if the user sits on the upper body, the upper body should lift the center of pelvic floor muscle of user and invert it in 'n' shape;
   a muscular force sensor on the upper or lower part of the support to sense force or pressure which presses the upper body down by the muscular contraction when the user contracts his/her inverted pelvic floor muscle;
   a controller to process data of the force or pressure sensed by the muscular force sensor and transmit the data outward to display them; and
   a height adjustor disposed between the upper body and the support,
   wherein the height adjustor is configured to adjust the height of the upper body to a desired height so that the press intensity against the pelvic floor muscle of user can be easily adjusted by the height adjustor;
   wherein the height adjustor comprises a first thread member extending upright from the support, a second thread member extending downward from the upper body and being engaged the first thread member, a recess formed on the bottom side of the support, and a handle positioned in the recess and connecting with the first thread member, and
   wherein the user can select between a passive electric stimulus through the electrodes and an active muscular exercise through the muscular force sensor.

2. An apparatus for strengthening pelvic floor muscles which comprises:
   an upper body of elongated shape for a user to sit on by perineum;
   a support supporting the upper body in the manner that, if the user sits on the upper body, the upper body should lift the center of pelvic floor muscle of the user and invert it in 'n' shape;
   a height adjustor positioned between the upper body and the support to adjust the height of the upper body, so that the press intensity against the pelvic floor muscle of the user can be adjusted;
   a muscular force transmitter connected to the upper end or lower end of the height adjustor and being parallel with the upper body;
   a muscular force sensor connected to the front end and rear end respectively to sense force or pressure which presses the upper body down by the muscular contraction when the user contracts his/her inverted pelvic floor muscle; and
   a controller to treat data of force or pressure sensed by the muscular force sensor and transmit the data outward to display them,
   wherein the height adjustor comprises a first thread member extending upright from the support, a second thread member extending downward from the upper body and being engaged with the first thread member, a recess formed on the bottom side of the support, and a handle positioned in the recess and connecting with the first thread member.

\* \* \* \* \*